US006313361B1

United States Patent
Waycuilis

(10) Patent No.: US 6,313,361 B1
(45) Date of Patent: Nov. 6, 2001

(54) FORMATION OF A STABLE WAX SLURRY FROM A FISCHER-TROPSCH REACTOR EFFLUENT

(75) Inventor: John J. Waycuilis, Cypress, TX (US)

(73) Assignee: Marathon Oil Company, Findlay, OH (US)

(*) Notice: Subject to any disclaimer, the term of this patent is extended or adjusted under 35 U.S.C. 154(b) by 0 days.

(21) Appl. No.: 09/135,625

(22) Filed: Aug. 18, 1998

Related U.S. Application Data

(60) Continuation of application No. 08/960,297, filed on Oct. 29, 1997, which is a division of application No. 08/600,565, filed on Feb. 13, 1996, now Pat. No. 5,733,941, which is a continuation-in-part of application No. 08/800,642, filed on Feb. 14, 1997, which is a continuation-in-part of application No. 08/600,565, filed on Feb. 13, 1996, now Pat. No. 5,733,941.

(51) Int. Cl.[7] .............................. C07C 2/00; C07C 27/00
(52) U.S. Cl. ........................ 585/314; 518/703; 518/705; 137/13
(58) Field of Search ................................. 518/703, 704, 518/705; 252/373; 137/13; 585/314

(56) References Cited

U.S. PATENT DOCUMENTS

| Re. 30,281 | 5/1980 | Tackett et al. ........................ 137/13 |
|---|---|---|
| 2,552,308 | 8/1951 | Buchmann et al. ............. 260/449.6 |
| 2,660,032 | 11/1953 | Rosenthal .......................... 60/39.02 |
| 2,686,195 | 8/1954 | McAdams et al. ............... 260/449.6 |
| 3,804,752 | 4/1974 | Merrill, Jr. et al. ................. 208/370 |
| 3,846,279 | 11/1974 | Merrill, Jr. et al. ................. 208/93 |
| 3,853,356 | 12/1974 | Merrill, Jr. et al. ................. 302/66 |
| 3,866,411 | 2/1975 | Marion et al. ..................... 60/39.02 |
| 3,868,817 | 3/1975 | Marion et al. ..................... 60/39.02 |
| 3,880,177 | 4/1975 | Kersch ................................ 137/13 |
| 3,900,041 | 8/1975 | Kersch et al. ...................... 137/13 |
| 3,900,391 | 8/1975 | Merrill, Jr. et al. ................. 208/370 |
| 3,910,299 | 10/1975 | Tackett et al. ....................... 137/13 |
| 3,920,579 | 11/1975 | Slater ................................... 252/373 |
| 3,950,034 | 4/1976 | Dreher et al. ........................ 302/66 |
| 3,959,072 | 6/1976 | Rudolf et al. ........................ 60/651 |
| 3,986,349 | 10/1976 | Egan .................................. 60/39.02 |
| 3,991,816 | 11/1976 | Klaren ................................. 165/1 |
| 4,008,924 | 2/1977 | Gogarty et al. ...................... 302/66 |
| 4,013,544 | 3/1977 | Merrill, Jr. et al. ................. 208/93 |
| 4,054,507 | 10/1977 | Pouska ................................. 208/24 |
| 4,074,981 | 2/1978 | Slater ................................. 48/197 R |
| 4,075,831 | 2/1978 | McGann ............................ 60/39.05 |
| 4,092,825 | 6/1978 | Egan .................................. 60/39.02 |
| 4,121,912 | 10/1978 | Barber et al. ...................... 48/197 R |
| 4,132,065 | 1/1979 | McGann ............................ 60/39.02 |
| 4,149,756 | 4/1979 | Tackett, Jr. ........................... 302/66 |
| 4,158,680 | 6/1979 | McGann ............................ 261/149 |
| 4,220,193 | 9/1980 | Klaren ................................. 165/1 |
| 4,309,359 | 1/1982 | Pinto .................................. 518/705 |
| 4,310,011 | 1/1982 | Tackett, Jr. ........................... 137/13 |
| 4,338,292 | 7/1982 | Duranleau .......................... 423/656 |
| 4,398,594 | 8/1983 | Klaren ............................ 165/104.16 |
| 4,434,613 | 3/1984 | Stahl et al. ......................... 60/39.07 |
| 4,502,919 | 3/1985 | Brunner et al. .................. 196/14.52 |
| 4,513,160 | 4/1985 | Avidan et al. ....................... 586/640 |
| 4,618,451 | 10/1986 | Gent ................................... 252/373 |
| 4,678,723 | 7/1987 | Wertheim ............................ 429/17 |
| 4,708,812 | 11/1987 | Hatfield .............................. 252/70 |
| 4,732,092 | 3/1988 | Gould ................................. 110/229 |
| 4,832,819 | 5/1989 | Hammer .............................. 208/27 |
| 4,833,170 | 5/1989 | Agee .................................. 518/703 |
| 4,946,477 | 8/1990 | Perka et al. ...................... 48/197 R |
| 4,973,453 | 11/1990 | Agee .................................. 422/190 |
| 5,026,934 | 6/1991 | Bains et al. ......................... 588/314 |
| 5,177,114 | 1/1993 | Van Dijk et al. ................... 518/703 |
| 5,245,110 | 9/1993 | Van Dijk et al. ................... 585/946 |
| 5,295,356 | 3/1994 | Billy .................................... 62/20 |
| 5,378,348 | 1/1995 | Davis et al. ......................... 208/27 |
| 5,472,986 | 12/1995 | van Dijk ............................ 518/705 |

FOREIGN PATENT DOCUMENTS

| 0 497 425 A1 | 8/1992 | (EP) . |
|---|---|---|
| 4-364142 | 12/1992 | (JP) . |

OTHER PUBLICATIONS

"Fluidized–Bed Heat Exchanger Avoids Fouling Problems", Chemical Engineering, Feb. 1988, p. 43.

Klaren et al., "The Non–Fouling Fluidized Bed Heat Exchanger", American Society of Mechanical Engineers, Heat Transfer Equipments Fundamentals, Design, Applications and Operating Problems, vol. 108, Book No. H00500, Jan. 1989, p. 273–279.

"Consider Nonfouling Fluidized Bed Echangers", Hydrocarbon Processing, Jul. 1989, pp. 48–50.

"Indirect Liquefaction; Contractor's Review Meeting Proceedings", U.S. Department of Energy, Nov. 1990, p. 283–290.

Hedden, K., et al., "A New Concept for the Production of Liquid Hydrocarbons from Natural Gas in Remote Areas", Oil Gas—European Magazine, Mar. 1994, pp. 42–44.

"The Syntroleum Process" promotional flier. Aug., 1994.

*Primary Examiner*—Johann Richter
*Assistant Examiner*—Sreeni Padmanabhan
(74) *Attorney, Agent, or Firm*—Jack E. Ebel

(57) ABSTRACT

A process is provided for treating a liquid effluent from a gas to liquid conversion reactor. A synthesis gas is initially converted to a liquid hydrocarbon phase in the gas to liquid conversion reactor. The liquid hydrocarbon phase includes a heavier liquid paraffinic wax compound and a lighter liquid paraffinic compound. The liquid hydrocarbon phase is discharged from the gas to liquid conversion reactor in a reactor effluent and an abrasive solid particle medium is entrained in the reactor effluent to form a fluidizable mixture. The reactor effluent is conveyed past a heat transfer surface which is cooler than the reactor effluent. The fluidizable mixture is contacted with the heat transfer surface and the liquid hydrocarbon phase is cooled to a temperature below the melting point of the heavier liquid paraffinic wax compound. Consequently, the heavier liquid paraffinic wax compound is converted to a plurality of unconsolidated solid wax particles. A slurry is formed from the plurality of unconsolidated solid wax particles and the remaining lighter liquid paraffinic compound.

21 Claims, 2 Drawing Sheets

FORMATION OF A STABLE WAX SLURRY FROM A FISCHER-TROPSCH REACTOR EFFLUENT

CROSS REFERENCES

This is a continuation in part of my U.S. patent application Ser. No. 08/960,297 filed on Oct. 29, 1997, which is a divisional of U.S. patent Ser. No. 08/600,565 filed on Feb. 13, 1996, now U.S. Pat. No. 5,733,941. This is also a continuation in part of my U.S. patent application Ser. No. 08/800,642 filed on Feb. 14, 1997, which is a continuation in part of U.S. patent Ser. No. 08/600,565 filed on Feb. 13, 1996, now U.S. Pat. No. 5,733,941.

TECHNICAL FIELD

The present invention relates generally to a process for converting a gaseous hydrocarbon to a synthetic liquid hydrocarbon and, more particularly, to a process for producing a stable wax slurry from the liquid effluent of a Fischer-Tropsch reactor.

BACKGROUND OF THE INVENTION

Processes for converting light hydrocarbon gases, such as natural gas, to heavier synthetic liquid hydrocarbons are generally known in the prior art. Such processes typically involve the "indirect" conversion of gaseous methane to liquid paraffinic hydrocarbon compounds, for example, as disclosed in U.S. Pat. No. 4,833,170. In accordance with the "indirect" conversion process of U.S. Pat. No. 4,833,170, the methane is first converted to a synthesis gas containing hydrogen and carbon monoxide by autothermal reforming, wherein the methane is reacted in a reformer with air in the presence of steam. The synthesis gas is then conveyed to a Fischer-Tropsch reactor which houses a hydrocarbon synthesis catalyst. The synthesis gas is converted to a liquid in the presence of the hydrocarbon synthesis catalyst and the resulting liquid effluent is discharged from the Fischer-Tropsch reactor. The liquid effluent comprises a hydrocarbon phase and an aqueous phase, with the paraffinic hydrocarbon compounds retained in the hydrocarbon phase. The hydrocarbon phase is separated from the aqueous phase upon discharge of the liquid effluent from the Fischer-Tropsch reactor and the synthetic paraffinic hydrocarbon compounds are recovered from the hydrocarbon phase as the liquid hydrocarbon product.

Although an often stated objective of prior art Fischer-Tropsch processes is to reduce the fraction of waxes produced within the mix of liquid paraffinic hydrocarbon compounds, in practice, many prior art Fischer-Tropsch processes, nevertheless, produce a significant fraction of waxes. Waxes are generally defined as relatively heavy paraffinic hydrocarbon compounds having a carbon number in excess of twenty, which are typically in a solid state at ambient temperatures. The presence of waxes in the liquid effluent from the Fischer-Tropsch reactor poses a substantial problem with respect to subsequent handling and transporting of the liquid hydrocarbon product because the waxes tend to coalesce and solidify as the liquid hydrocarbon product cools to ambient temperature. The solid waxes render the hydrocarbon product considerably more difficult to handle and transport, for example, via tanker transport vehicles or product distribution pipelines which are susceptible to fouling and plugging in the presence of solid waxes. One solution to this problem is to maintain the liquid hydrocarbon product at a temperature above the melting point of the waxes at all times. However, this solution is energy-intensive and, therefore, relatively costly. An alternate solution is to perform hydrotreating and mild hydrocracking of the liquid hydrocarbon product after it exits the Fischer-Tropsch reactor to break down the long chain waxes into shorter chain hydrocarbons which remain liquid at ambient temperatures. However, this solution is capital-intensive and likewise relatively costly.

The present invention recognizes a need for a cost-effective solution to the problem of handling and transporting a liquid hydrocarbon product discharged from a Fischer-Tropsch reactor which has a significant fraction of waxes. Accordingly, it is an object of the present invention to provide a process for treating the liquid effluent of a Fischer-Tropsch reactor to facilitate subsequent handling and transportation of the hydrocarbon phase contained in the liquid effluent. More particularly, it is an object of the present invention to provide a treatment process for the liquid effluent of a Fischer-Tropsch reactor, wherein a stable slurry comprising heavier solid hydrocarbon waxes and lighter liquid hydrocarbon compounds is formed from the liquid effluent. It is another object of the present invention to provide a treatment process for the liquid effluent of a Fischer-Tropsch reactor, wherein the resulting slurry is readily transportable via tanker transport vehicles or distribution pipelines at ambient temperatures. It is another object of the present invention to provide a treatment process for the liquid effluent of a Fischer-Tropsch reactor, wherein the slurry is formed from the liquid effluent in a single cost-effective processing step. It is yet another object of the present invention to provide a treatment process for the liquid effluent of a Fischer-Tropsch reactor, wherein the slurry is formed from the liquid effluent by cooling the liquid effluent in a fluidized bed heat exchanger. It is still another object of the present invention to provide a treatment process for the liquid effluent of a Fischer-Tropsch reactor, wherein an aqueous liquid phase is separated from the liquid effluent during formation of the slurry to reduce the amount of water in the slurry. These objects and others are achieved in accordance with the invention described hereafter.

SUMMARY OF THE INVENTION

The present invention is a process for treating a liquid effluent from a gas to liquid conversion reactor. The process comprises feeding a synthesis gas to the gas to liquid conversion reactor and converting the synthesis gas to a liquid hydrocarbon phase therein. The liquid hydrocarbon phase comprises at least one heavier liquid paraffinic wax compound and at least one lighter liquid paraffinic compound. The liquid hydrocarbon phase is discharged from the gas to liquid conversion reactor in a reactor effluent, which further comprises a liquid aqueous phase and a gas phase. The gas phase is separated from the reactor effluent and thereafter an abrasive solid particle medium is entrained in the reactor effluent to form a fluidizable mixture. In a preferred embodiment, the abrasive solid particle medium is fluidized in the reactor effluent to form a fluidized bed.

The reactor effluent is conveyed through the interior of a heat transfer tube, which is enclosed within a heat transfer shell having a heat transfer medium maintained therein. The tube wall constitutes a heat transfer surface which is cooler than the reactor effluent. The fluidizable mixture is contacted with the tube wall, cooling the liquid hydrocarbon phase to a temperature below the melting point of the heavier liquid paraffinic wax compound. Consequently, at least a portion of the at least one heavier liquid paraffinic wax compound is converted to a plurality of unconsolidated solid wax particles. The solid particle medium displaces any solid wax particles which accumulate on the tube wall as the liquid effluent passes through the tube interior. Upon exiting the tube interior, the liquid aqueous phase is separated from the reactor effluent. A slurry is formed from the plurality of unconsolidated solid wax particles and the at least one lighter liquid paraffinic compound remaining in the liquid hydrocarbon phase of the reactor effluent. The slurry is subsequently stored and/or transported via a tanker transport vehicle or a distribution pipeline.

The invention will be further understood from the accompanying drawings and description.

DESCRIPTION OF PREFERRED EMBODIMENTS

The present invention is a liquid effluent treatment process which is practiced as a downstream adjunct to a process for converting a hydrocarbon gas to synthetic liquid hydrocarbons. For purposes of illustration, the practice of the present liquid effluent treatment process is described below in conjunction with a specific gas to liquid conversion process, which employs a Fischer-Tropsch reactor as disclosed in U.S. Pat. No. 5,733,941, incorporated herein by reference. However, it is understood that practice of the present liquid effluent treatment process is not limited to any specific gas to liquid conversion process. For example, the present liquid effluent treatment process may likewise be practiced as an adjunct to the gas to liquid conversion processes disclosed in U.S. Pat. Nos. 4,833,170; 2,552,308; or 2,686,195, all incorporated herein by reference.

Figure 1:
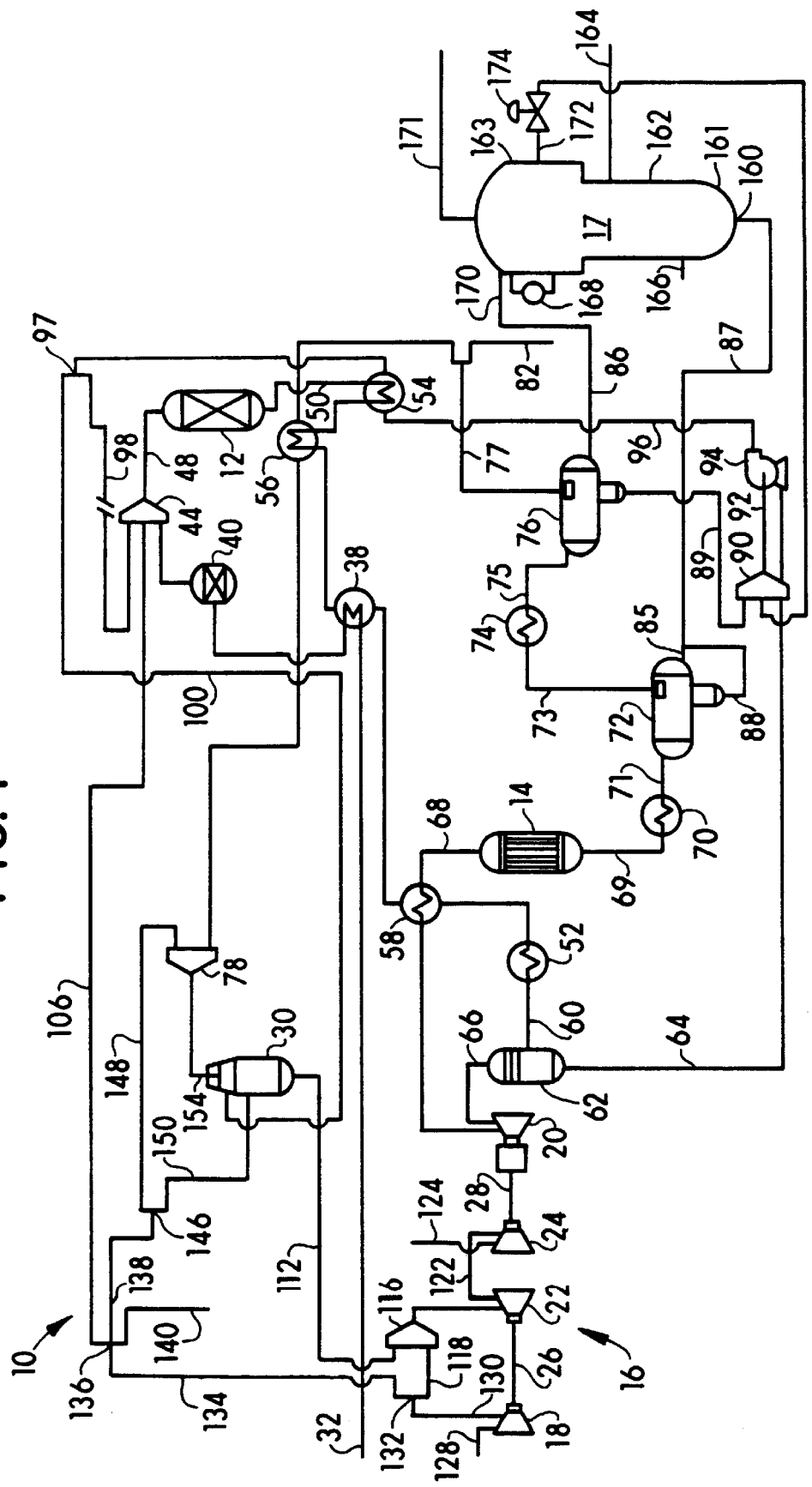
FIG. 1 is a schematic view of a system for practicing a gas to liquid conversion process and an associated liquid effluent treatment process of the present invention.

Referring to FIG. 1, a system is shown and generally designated 10, which has utility in the practice of the gas to liquid conversion process and the associated liquid effluent treatment process of the present invention. The system 10 comprises four primary operational units: an autothermal reformer (ATR) 12, a Fischer-Tropsch reactor (F/T reactor) 14, a Brayton cycle 16, and a fluidized bed heat exchanger (FBHX) 17. The ATR 12, F/T reactor 14, and Brayton cycle 16 are employed in the practice of the gas to liquid conversion process. The FBHX 17 is employed in the practice of the associated liquid effluent treatment process. More particularly, the ATR 12 is provided to reform a hydrocarbon feed gas, compressed air and steam into a synthesis gas. The F/T reactor 14 is provided to convert the synthesis gas to a synthetic liquid hydrocarbon. The Brayton cycle 16 is provided to compress the air feed to the ATR 12, utilizing power generated by combustion of the F/T reactor tail gas. The Brayton cycle 16 includes a pair of compressors 18, 20, a pair of power turbines 22, 24 mechanically linked by shafts 26, 28 to the compressors 18, 20, respectively, and a combustor 30 that supplies a combustion gas to the power turbines 22, 24. The FBHX 17 is provided to cool the liquid effluent from the F/T reactor 14 and convert the liquid effluent to a stable wax slurry.

The system 10 specifically comprises a hydrocarbon feed gas line 32 through which a hydrocarbon feed gas is supplied to the system 10. The hydrocarbon feed gas is preferably natural gas, although other hydrocarbon feed gases have utility herein, including subquality gas containing nitrogen and/or carbon dioxide, gas derived from coal seams or gas derived from ocean hydrates. The hydrocarbon feed gas line 32 conveys the hydrocarbon feed gas downstream in the direction of the ATR 12. Also serially positioned in the hydrocarbon feed gas line 32 are a hydrocarbon feed gas heat exchanger 38 and an $H_2S$ removal unit 40. The hydrocarbon feed gas heat exchanger 38 preheats the hydrocarbon feed gas by means of a high-temperature synthesis gas exiting the ATR 12, as described hereafter. The $H_2S$ removal unit 40 is a zinc oxide bed that substantially removes all $H_2S$ present in the preheated hydrocarbon feed gas.

The hydrocarbon feed gas line 32 extends to an ATR carburetor 44. Air and steam also feed into the ATR carburetor 44 from an air and steam source described hereafter. The ATR carburetor 44 mixes the hydrocarbon feed gas from the hydrocarbon feed gas line 32 with the air and steam and an ATR inlet gas mixture line 48 exits the ATR carburetor 44 carrying the gaseous mixture comprising the hydrocarbon feed gas, air and steam (termed the ATR inlet gas mixture) from the ATR carburetor 44 to the ATR 12.

The ATR 12 is a high-temperature reactor vessel, wherein the ATR inlet gas mixture is adiabatically reacted to produce a synthesis gas containing $H_2$ and CO. Adiabatic reaction of the ATR inlet gas mixture comprises partially combusting the hydrocarbon feed gas to exothermically oxidize a portion thereof and contacting the methane component of the hydrocarbon feed gas with steam in the presence of a steam reforming catalyst, such as nickel-containing catalysts, to endothermically reform the methane and steam.

An ATR outlet line 50 removes the synthesis gas, preferably having a molar composition of about 2.0 moles of hydrogen per mole of carbon monoxide, from the ATR 12. The ATR outlet line 50 conveys the synthesis gas from the ATR 12 to an ATR condenser 52. Serially positioned in the ATR outlet line 50 upstream of the ATR condenser 52 are a plurality of heat exchangers including a steam conversion heat exchanger 54, a separator tail gas heat exchanger 56, the hydrocarbon feed gas heat exchanger 38, and an F/T reactor feed gas heat exchanger 58. The steam conversion heat exchanger 54 utilizes the high-temperature synthesis gas exiting the ATR 12 to heat process water for steam conversion, while quenching the synthesis gas. The separator tail gas heat exchanger 56 utilizes the high-temperature synthesis gas to heat a tail gas exiting a product separator described hereafter downstream of the F/T reactor 14. The hydrocarbon feed gas heat exchanger 38 utilizes the high-temperature synthesis gas to heat the hydrocarbon feed gas to the ATR 12 as described above. The F/T reactor feed gas heat exchanger 58 utilizes the high-temperature synthesis gas to heat the synthesis gas to the F/T reactor 14.

The ATR outlet line 50 feeds the synthesis gas into the ATR condenser 52, which cools the synthesis gas, condensing the water contained therein. A condenser outlet line 60 conveys the resulting mixture of cooled synthesis gas and water from the ATR condenser 52 to a scrubber 62 where the water is separated from the synthesis gas. A scrubber water outlet line 64 withdraws the water from the bottom of the scrubber 62 for conversion to steam and return to the system 10. A scrubber gas outlet line 66 withdraws the cooled synthesis gas from the top of the scrubber 62. The scrubber gas outlet line 66 conveys the cooled synthesis gas to the synthesis gas compressor 20 of the Brayton cycle 16.

The synthesis gas compressor 20 is driven by the shaft 28 connected to the second stage power turbine 24 which is driven by means described hereafter. The synthesis gas compressor 20 compresses the synthesis gas and an F/T reactor inlet line 68 conveys the compressed synthesis gas from the synthesis gas compressor 20 to the F/T reactor 14. The F/T reactor feed gas heat exchanger 58 described above preheats the compressed synthesis gas before the synthesis gas is fed to the F/T reactor 14. The F/T reactor 14 is typically one or more packed tubular reactors in series or alternatively the F/T reactor 14 is a fluidized bed reactor. In any case, the F/T reactor 14 is preferably charged with a cobalt-containing catalyst and is maintained at nearly isothermal conditions by means such as externally cooling the F/T reactor 14 with boiling water or some other cooling medium to remove the exothermic heat of reaction, thereby reacting the CO and $H_2$ of the synthesis gas to form water and heavy hydrocarbons therefrom.

An F/T reactor outlet line 69 withdraws the entire F/T reactor effluent from the F/T reactor 14 which comprises a mixture of lighter and heavier liquid hydrocarbon compounds, as well as nitrogen and steam. The molar conversion of carbon monoxide in the F/T reactor 14 to hydrocarbon compounds is preferably about 90%. A typical F/T reactor effluent production rate from the F/T reactor 14 is about 35,000 to 52,000 kg/hr at a temperature in a range of about 200 to 240° C. and a pressure in a range of about 1,600 to 2,800 kPa. The F/T reactor outlet line 69 feeds the F/T reactor effluent to an F/T reactor cooler 70 where the F/T reactor effluent is cooled, thereby partially condensing the F/T reactor effluent to form a first effluent mixture comprising a two-phase liquid portion and a vapor phase portion. The two-phase liquid comprises a heavy liquid hydrocarbon phase, containing heavier paraffinic wax compounds and lighter paraffinic compounds, and a first liquid aqueous phase containing water.

The first effluent mixture discharged from the F/T reactor cooler 70 is typically at a a pressure in a range of about 1,500 to 2,700 kPa and at a temperature in a range of about 60 to 100° C. In any case, the temperature of the first effluent mixture is at least about 5° C. greater than the temperature at which a significant portion of the heavier paraffinic wax compounds contained therein would solidify. An F/T reactor cooler outlet line 71 conveys the first effluent mixture to a vapor separator 72.

The vapor separator 72 initiates the liquid effluent treatment process of the present invention by separating the first effluent mixture into the vapor phase, the heavy liquid hydrocarbon phase and the first liquid aqueous phase. A vapor outlet line 73, a heavy liquid hydrocarbon outlet line 85, and an aqueous outlet line 88 withdraw the vapor, heavy liquid hydrocarbon and first liquid aqueous phases from the vapor separator 72, respectively. The weight ratio of the vapor phase to the combined liquid phases is in a range of about 3:1 to 6:1. The aqueous outlet line 88 joins with the heavy liquid hydrocarbon outlet line 85 downstream of the vapor separator 72 to form a liquid effluent line 87. The first liquid aqueous phase mixes with the heavy liquid hydrocarbon phase in the liquid effluent line 87 producing a liquid effluent. The volumetric ratio of the heavy liquid hydrocarbon phase to the first liquid aqueous phase in the liquid effluent is in a range of about 0.3:1 to 1:1. The heavy liquid hydrocarbon phase contains substantially all of the heavier paraffinic wax compounds and a portion of the lighter paraffinic compounds produced in the F/T reactor 14. The heavy liquid hydrocarbon phase preferably has a composition resembling that of a highly paraffinic crude oil as, for example, represented by the following volumetric composition ranges: 5 to 10% naphtha, 50 to 80% distillate, 10 to 35% lube stock and 5 to 30% wax compounds, depending on the catalyst and F/T reactor 14 conditions. The liquid effluent treatment process proceeds with treatment of the heavy liquid hydrocarbon and first liquid aqueous phases in a manner described hereafter, while the vapor phase is treated as follows.

The vapor outlet line 73 conveys the vapor phase to an F/T reactor condenser 74 at a rate of about 26,000 to 45,000 kg/hr, a temperature in a range of about 60 to 100° C. and a pressure in a range of about 1,500 to 2,700 kPa. The vapor phase is further cooled in the F/T reactor condenser, thereby forming a second effluent mixture comprising a gas phase portion and a two-phase liquid portion, which includes a light liquid hydrocarbon phase containing lighter paraffinic hydrocarbon compounds, and a second liquid aqueous phase containing water. An F/T reactor condenser outlet line 75 conveys the second effluent mixture to a phase separator 76 where the gas phase, light liquid hydrocarbon phase, and second aqueous phase are separated from one another. The volumetric ratio of the light liquid hydrocarbon phase to the second liquid aqueous phase is in a range of about 0.5:1 to 2:1. A light liquid hydrocarbon outlet line 86 withdraws the light liquid hydrocarbon phase from the phase separator 76 at a rate of about 50 to 1,500 kg/hr, a temperature in a range of about −30 to 60° C. and a pressure in a range of about 1,450 to 2,650 kPa. The light liquid hydrocarbon phase has an exemplary composition represented by the following volumetric composition ranges: 0–15% LPG, 1–40% naphtha, 45–99% distillate and 0–1% wax compounds.

The light liquid hydrocarbon outlet line 86 conveys the light liquid hydrocarbon phase to the FBHX 17 in a manner described hereafter. In accordance with an alternate embodiment not shown, the light liquid hydrocarbon outlet line 86 is returned to the liquid effluent line 87 where the light liquid hydrocarbon phase is combined with the heavy liquid hydrocarbon phase before entering the FBHX 17. In accordance with yet another alternate embodiment not shown, the light liquid hydrocarbon outlet line 86 is directed to an independent product recovery means where the light liquid hydrocarbon phase is recovered as a separate product.

A separator tail gas outlet line 77 withdraws the gas phase of the second effluent mixture as a separator tail gas from the top of the phase separator 76 at a typical rate of about 22,000 to 32,000 m³/hr, a temperature in a range of about −30 to 60° C., and a pressure in a range of about 1,450 to 2,650 kPa. The separator tail gas comprises nitrogen, carbon monoxide, hydrogen, water and light hydrocarbons typically having a molar composition range of about 80–90% $N_2$, 5–10% $CO_2$, 2–5% CO, 1–5% $H_2$, 0–1% $H_2O$, and the remainder hydrocarbons. As such, the separator tail gas has a relatively low heating value in the range of about 1,500 to 3,000 kJ/kg. The separator tail gas outlet line 77 extends from the phase separator 76 to a combustor inlet mixer 78 described hereafter. The separator tail gas outlet line 77 is provided with the separator tail gas heat exchanger 56 which elevates the temperature of the separator tail gas using the high-temperature synthesis gas from the ATR outlet line 50 as the heat transfer medium. An excess tail gas line 82 is provided in the separator tail gas outlet line 77 upstream of the separator tail gas heat exchanger 56 which enables withdrawal of excess separator tail gas from the system 10 during process start-up or in response to process upsets. A flare (not shown) external to the system 10 is provided to dispose of the excess separator tail gas.

A vapor separator water outlet line 89 withdraws the second liquid aqueous phase from the phase separator 76 and conveys the water to a pump inlet manifold 90 where it combines with the water from the scrubber water outlet line 64 and exits the pump inlet manifold 90 via a pump inlet line 92. The pump inlet line 92 conveys the water to a multi-stage centrifugal pump 94 which elevates the pressure of the water therein and discharges the pressurized water to a pump outlet line 96. The steam conversion heat exchanger 54 is provided in the pump outlet line 96 to heat the pressurized water therein, using the high-temperature synthesis gas from the ATR outlet line 50 as the heat transfer medium. The steam conversion heat exchanger 54 elevates the temperature of the pressurized water, thereby converting the water in the pump outlet line 96 to steam. The pump outlet line 96 splits at a junction point 97 downstream of the steam conversion heat exchanger 54 into an ATR steam inlet line 98 and a combustor steam inlet line 100. The ATR steam inlet line 98 extends to the ATR carburetor 44, which joins the ATR steam inlet line 98, the hydrocarbon feed gas line 32 and an ATR air inlet line 106.

The combustor steam inlet line 100 extends from the junction point 97 to the combustor 30. A combustor outlet line 112 conveys a combustor gas/steam mixture formed in the combustor 30 to a power turbine inlet gas return manifold 116. The power turbine inlet gas return manifold 116 joins the combustor outlet line 112 to the first stage power turbine 22. A cooling air inlet 118 internal to the power turbine 22 conveys cooling air into the power turbine blades and discs (not shown). Accordingly, a combustor gas/steam/air mixture flows through the first stage power turbine 22 as the drive gas for the first stage power turbine 22. The shaft 26 mechanically links the first stage power turbine 22 to the air compressor 18, thereby driving the air compressor 18.

A first stage power turbine outlet 122 conveys spent first stage drive gas from the first stage power turbine 22 to the second stage power turbine 24 which becomes the drive gas for the second stage power turbine 24. The shaft 28 mechanically links the second stage power turbine 24 to the synthesis gas compressor 20. The shaft 28 may also be mechanically linked to an electrical generator (not shown) providing electric power for other on-site uses and/or for export. A second stage power turbine outlet line 124 conveys spent second stage drive gas from the second stage power turbine 24 to a flue (not shown) which exhausts the spent second stage drive gas from the system 10.

The system 10 further comprises an air feed inlet 128 through which an air feed is supplied directly to the air compressor 18. An air compressor outlet 130 internal to the air compressor 18 conveys the compressed air feed to a junction point 132 where the air compressor outlet 130 splits into the cooling air inlet 118 and an air takeoff line 134. The cooling air inlet 118 conveys its portion of the compressed air feed to the blades and discs of the first stage power turbine 22 as described above. The air takeoff line 134 conveys the remainder of the compressed air feed to a first air junction point 136 where the air takeoff line 134 splits into the ATR air inlet line 106, a combustion air line 138, and an air bleed line 140. The air bleed line 140 normally has no flow therethrough except in the event of an excess pressure build-up in the air takeoff line 134 during start-up, upset conditions or at low feed rates of the hydrocarbon feed gas.

The combustion air line 138 extends from the first air junction point 136 to a second air junction point 146 where the combustion air line 138 splits into a primary air combustor inlet line 148 and a secondary air combustor inlet line 150. The primary air combustor inlet line 148 provides a sufficient air feed to maintain combustion within the combustor 30. The combustor inlet mixer 78 joins the primary combustor air inlet line 148 with the separator tail gas outlet line 77 to mix the gas streams of the lines 148 and 77 therein.

A combustor inlet burner assembly 154 exits the combustor inlet mixer 78 and extends into the combustor 30. The combustor inlet burner assembly 154 injects the gaseous mixture of the primary air feed and separator tail gas, termed the combustor feed gas, to the combustor 30 for combustion therein. The secondary air combustor inlet line 150 conveys the secondary air feed for injection into the combustor 30. The secondary air feed oxidizes the remainder of the combustibles in the combustor 30, while diluting and cooling the combustor gas/steam/air mixture exiting the combustor to the power turbine inlet manifold 116. The combustor gas/steam/air feed is cooled to a temperature below the maximum temperature allowable in the first stage power turbine 22. The combustor 30 is a high temperature vessel which may contain a catalyst to promote the combustion reactions therein. The ATR air inlet line 106 extends from the junction point 136 to the ATR carburetor 44 described above and conveys its remaining portion of the remaining compressed air feed to the ATR carburetor 44.

In accordance with the liquid effluent treatment process of the present invention, the liquid effluent having the above-described composition is conveyed via the liquid effluent line 87 at a rate of about 5,000 to 10,000 kg/hr, a temperature in a range of about 60 to 100° C., and a pressure in a range of about 1,500 to 2,700 kPa to an FBHX liquid effluent inlet 160 in a lower chamber 161 of the FBHX 17. The liquid effluent is conveyed upward through the lower chamber 161 and, thereafter, through a middle chamber 162 of the FBHX 17, defining a heat transfer zone, into an upper chamber 163 of the FBHX 17, defining a freeboard. A coolant is simultaneously conveyed downward through the middle chamber 162 in a countercurrent manner from an FBHX coolant inlet line 164 to an FBHX coolant outlet line 166. The coolant can be substantially any conventional heat transfer medium and is preferably a liquid heat transfer medium selected from among water, glycol-water mixtures, mineral oil, or other conventional commercially available heat transfer liquids.

The coolant is conveyed into the FBHX 17 at a rate of about 2,500 to 10,000 kg/hr, a temperature in a range of about 5 to 50° C., and a pressure in a range of about 150 to 500 kPa. The coolant cools the liquid effluent in the middle chamber 162 from the above-recited temperature range to a cooled temperature range of about 10 to 55° C. Wax compounds make up about 5 to 30% by weight of the heavy liquid hydrocarbon phase. The cooled temperature of the liquid effluent is at a level below the melting point of at least a portion of the wax compounds and the cooled temperature is preferably as close as practical to the minimum ambient temperature the wax slurry product is ultimately likely to experience during subsequent storage or transport. Consequently, cooling the liquid effluent causes at least a portion, and preferably at least about 50% by weight, of the wax compounds in the heavy liquid hydrocarbon phase to solidify into a plurality of unconsolidated solid wax particles. The solid wax particles are typically within a size range of about 0.1 to 5 mm.

The heavy liquid hydrocarbon phase and first liquid aqueous phase separate in the upper chamber 163, with the unconsolidated solid wax particles remaining suspended in the heavy liquid hydrocarbon phase which is substantially free of water. A level controller 168 is provided in the upper chamber 163 to regulate the level of the interface 169 between the heavy liquid hydrocarbon phase and first liquid aqueous phase (shown in FIG. 2). The light hydrocarbon outlet line 86 feeds the light liquid hydrocarbon phase to the upper chamber 163 at a level above the interface 169 via a light liquid hydrocarbon inlet 170 where the light liquid hydrocarbon phase mixes with the heavy liquid hydrocarbon phase. The light liquid hydrocarbon phase is fed to the upper chamber 163 at a rate of about 50 to 1,500 kg/hr, a temperature in a range of about −30 to 60° C., and a pressure in a range of about 1,450 to 2,650 kPa such that the weight ratio of the light liquid hydrocarbon phase to the heavy liquid hydrocarbon phase including the solid wax particles is in a range of about 0.02:1 to 0.5:1.

The light liquid hydrocarbon phase may be at a temperature below the cooled temperature of the heavy liquid hydrocarbon phase to subcool the heavy hydrocarbon phase and cause growth of the solid wax particles by the further deposition of wax compounds on the solid wax particles. In any case, the resulting mixture of unconsolidated solid wax particles and light and heavy liquid hydrocarbon phases forms a stable slurry, wherein the solid wax particles make up about 5 to 30% by volume of the slurry, the remainder being liquid hydrocarbons. The slurry is withdrawn from the upper chamber 163 via a slurry outlet line 171 at a rate of about 2,500 to 4,000 kg/hr, a temperature in a range of about 5 to 50° C., and a pressure in a range of about 500 to 2,500 kPa. The slurry is typically conveyed via the slurry outlet line 171 to a storage tank (not shown) before transport via a hydrocarbon product distribution pipeline or a tanker transport vehicle such as a truck or a ship. The first liquid aqueous phase, which is made up of water and is substantially free of wax and other hydrocarbon compounds, is withdrawn from the upper chamber 163 via an FBHX water outlet line 172 and conveyed to the pump inlet manifold 90. A valve 174 is provided in the FBHX water outlet line 172 to regulate fluid flow therethrough. The water in the FBHX water outlet line 172 is combined with the water from the vapor separator water outlet line 89 and scrubber water outlet line 64 at the pump inlet manifold 90 and fed to the pump inlet line 92 where the water is utilized in the gas to liquid conversion process as described above.

Figure 2:
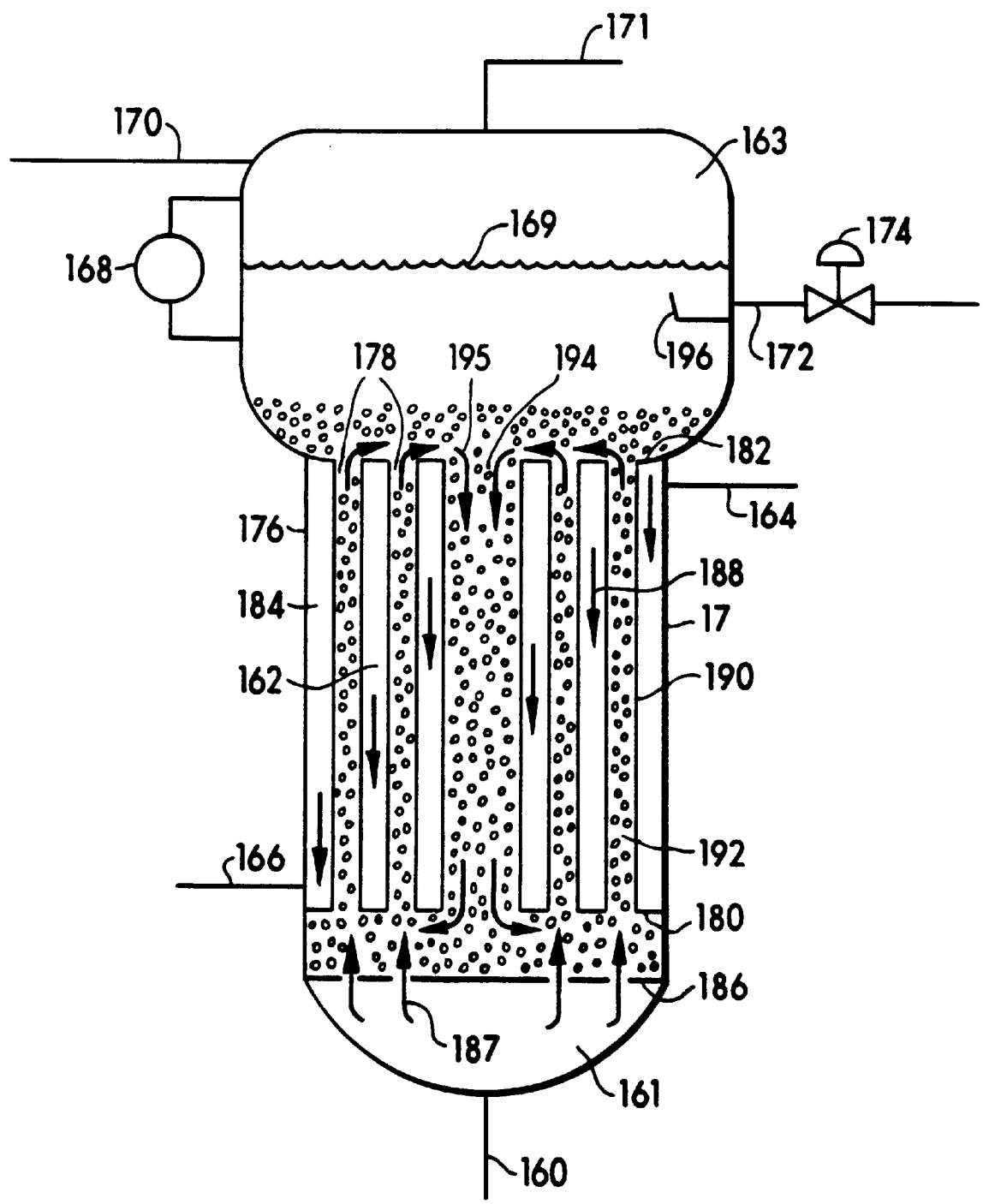
FIG. 2 is a conceptualized cross-sectional view of the fluidized bed heat exchanger shown in the system of FIG. 1 having utility in the liquid effluent treatment process of the present invention.

Referring to FIG. 2, the structure and operation of the FBHX 17 are described in greater detail. The FBHX 17 is substantially similar to those disclosed in U.S. Pat Nos. 3,991,816; 4,220,193; and 4,398,594, incorporated herein by reference, although the present FBHX 17 is specifically adapted for use in the liquid effluent process disclosed herein. As noted above, the FBHX 17 is provided with a liquid effluent inlet 160, a coolant inlet line 164, a coolant outlet line 166, a light liquid hydrocarbon inlet 170, a slurry outlet line 171, and an FBHX water outlet line 172. A shell 176 encloses the FBHX 17 defining a continuous vessel including the lower, middle, and upper, chambers 161, 162, 163. A plurality of substantially parallel open-ended vertical riser tubes 178 are disposed within the middle chamber 163 extending from a lower tube plate 180 to an upper tube plate 182. The tubes 178 are separated from one another, defining an interstitial space 184 through which coolant flow is enabled. The lower tube plate 180 and upper tube plate 182 define the lower and upper bounds of the middle chamber 162, respectively, and prevent fluid communication between the interstitial space 184 and the lower and upper chambers 161,163.

The liquid effluent is fed to the FBHX 17 via the liquid effluent inlet 160 which enters the lower chamber 161 at a point below a distributor plate 186. As the liquid effluent is conveyed upward through the distributor plate 186, it is uniformly distributed radially across the lower chamber 161 as shown by arrows 187. The liquid effluent continues upward from the lower chamber 161 into the tube openings at the lower tube plate 180, through the tubes 178 in the middle chamber 162, and out the tube openings at the upper tube plate 182 into the upper chamber 163. The coolant is simultaneously conveyed into the middle chamber 162 via the FBHX coolant inlet line 164 and passes downward through the interstitial space 184 until reaching the bottom of the middle chamber 162 where the coolant is discharged via the FBHX coolant outlet line 166 as shown by arrows 188. The coolant is in continuous contact with the outside of the tube walls 190 during its descent through the middle section 162, while the liquid effluent is in continuous contact with the inside of the tube walls 190 during its ascent through the middle section 162. The tube walls 190 are formed from a heat conductive material, which provides an effective heat transfer surface for the liquid effluent. As noted above, the coolant sufficiently cools the liquid effluent in the middle chamber 162 to cause at least a portion of the wax compounds in the heavy liquid hydrocarbon phase to solidify into a plurality of unconsolidated solid wax particles.

The liquid effluent is conveyed through the tubes 178 at a superficial velocity which substantially entrains a solid particle medium 192 residing within the tubes 178 and forms a fluidizable mixture comprising the liquid effluent and solid particle medium 192. The solid particle medium 192 is a plurality of divided particles formed from a hard abrasive material relative to the solid wax particles, such as chopped metal wire, gravel, or glass, ceramic or metal beads. The superficial velocity of the liquid effluent is sufficient to fluidize the solid particle medium 192 such that the liquid effluent constitutes the fluidizing medium and the entrained solid particle medium 192 constitutes the fluidized bed. The fluidized bed shown in FIG. 2 is a circulating bed, wherein the individual solid particle medium 192 of the bed flows from the bottom chamber 161 to the upper chamber 163 in correspondence with the liquid effluent. A downcomer 194 axially positioned within the middle chamber 162 enables auto-recirculation of the bed. In particular, when the solid particle medium 192 reaches the upper chamber 163, it is returned to the lower chamber 161 via the downcomer 194 as shown by arrows 195. Also encompassed within the scope of the present invention and embodied by the term "fluidized bed", as used herein, is a stationary bed (not shown), wherein the vertical position of each individual solid particle making up the bed remains relatively constant within the middle chamber 162. Whether the fluidized bed behaves as a stationary bed or a recirculating bed is a function of the superficial velocity and flow pattern selected by the practitioner and is within the purview of the skilled artisan.

In any case, the solid particle medium 192 experiences turbulent flow while it is fluidized within the tubes 178, causing the solid particle medium 192 to collide with the tube walls 190 and with the solid wax particles suspended in the liquid effluent. The collisions produce a scouring action, diminishing the ability of the solid wax particles to accumulate on the tube walls 190 and displacing any solid wax particles which adhere to the tube walls 190. Thus, the solid particle medium 192 substantially prevents or reduces fouling or plugging in the tubes 178 caused by solid wax particle build-up.

When the fluidizable mixture reaches the upper chamber 163, it is dissipated, with the solid particle medium 192 being returned to, or retained in, the middle chamber 162 and the heavy liquid hydrocarbon phase and first liquid aqueous phase separating from one another by gravity. The solid wax particles remain suspended in the heavy liquid hydrocarbon phase and added light liquid hydrocarbon phase, forming the stable wax slurry, which is withdrawn from the upper chamber 163 via the slurry outlet line 171.

The water making up the first liquid aqueous phase is withdrawn from the upper chamber 163 via the FBHX water outlet line 172 under the control of the valve 174. A sluice 196 is provided at the FBHX water outlet line 172 to inhibit the flow of the solid particle medium 192 and solid wax particles into the FBHX water outlet line 172. The level controller 168 insures that the level of the interface 169 between the heavy liquid hydrocarbon phase and first liquid aqueous phase remains above the level of the sluice 196.

While the foregoing preferred embodiments of the invention have been described and shown, it is understood that alternatives and modifications, such as those suggested and others, may be made thereto and fall within the scope of the present invention. For example, modifications to the Brayton cycle, as taught by U.S. Pat. No. 5,733,941, may likewise be applied to the above-described gas to liquid conversion process, which is practiced in association with the liquid effluent treatment process of the present invention.

I claim:

1. A process for treating a liquid effluent from a gas to liquid conversion reactor comprising:

feeding a synthesis gas to a gas to liquid conversion reactor;

converting said synthesis gas to a liquid hydrocarbon phase in said gas to liquid conversion reactor, wherein said liquid hydrocarbon phase comprises at least one heavier liquid paraffinic wax compound and at least one lighter liquid paraffinic compound;

discharging said liquid hydrocarbon phase from said gas to liquid conversion reactor in a reactor effluent;

entraining an abrasive solid particle medium in said reactor effluent to form a fluidizable mixture;

conveying said reactor effluent past a heat transfer surface while contacting said fluidizable mixture with said heat transfer surface, wherein said heat transfer surface is cooler than said reactor effluent;

cooling said liquid hydrocarbon phase upon contact with said heat transfer surface to convert at least a portion of said at least one heavier liquid paraffinic wax compound to a plurality of unconsolidated solid wax particles; and forming a slurry comprising said plurality of unconsolidated solid wax particles and said at least one lighter liquid paraffinic compound.

2. The process of claim 1, wherein reactor effluent comprises said liquid hydrocarbon phase and further comprises a liquid aqueous phase.

3. The process of claim 2 further comprising separating said liquid aqueous phase from said reactor effluent after cooling said liquid hydrocarbon phase.

4. The process of claim 1, wherein said liquid hydrocarbon phase is cooled to a cooled temperature below the melting point of said heavier liquid paraffinic wax compound.

5. The process of claim 1 further comprising conveying said slurry via a distribution pipeline or a transport vehicle.

6. The process of claim 1, wherein said reactor effluent further comprises a gas phase.

7. The process of claim 6 further comprising separating said gas phase from said reactor effluent before entraining said solid particle medium in said reactor effluent.

8. The process of claim 1, wherein solid particle medium displaces said solid wax particles from said heat transfer surface.

9. The process of claim 1, wherein said heat transfer surface is the wall of a tube having a tube interior, a tube exterior, a tube inlet and a tube outlet.

10. The process of claim 9, wherein said reactor effluent is conveyed through said tube interior.

11. The process of claim 2, wherein said heat transfer surface is the wall of a tube having a tube interior, a tube exterior, a tube inlet and a tube outlet.

12. The process of claim 11 further comprising separating said liquid aqueous phase and said liquid hydrocarbon phase after discharging said liquid effluent from said tube outlet.

13. A process for treating a liquid effluent from a gas to liquid conversion reactor comprising:

feeding a synthesis gas to a gas to liquid conversion reactor;

converting said synthesis gas to a liquid hydrocarbon phase in said gas to liquid conversion reactor, wherein said liquid hydrocarbon phase comprises at least one heavier liquid paraffinic wax compound and at least one lighter liquid paraffinic compound;

discharging said liquid hydrocarbon phase from said gas to liquid conversion reactor in a reactor effluent comprising said liquid hydrocarbon phase and a liquid aqueous phase;

fluidizing an abrasive solid particle medium in said reactor effluent to form a fluidized bed;

conveying said reactor effluent past a heat transfer surface while contacting said reactor effluent and said fluidized bed with said heat transfer surface, wherein said heat transfer surface is cooler than said reactor effluent;

cooling said liquid hydrocarbon phase upon contact with said heat transfer surface to convert at least a portion of said at least one heavier liquid paraffinic wax compound to a plurality of unconsolidated solid wax particles;

separating said liquid hydrocarbon phase and said liquid aqueous phase; and forming a slurry comprising said plurality of unconsolidated solid wax particles and said at least one lighter liquid paraffinic compound.

14. The process of claim 13, wherein said liquid hydrocarbon phase is cooled to a cooled temperature below the melting point of said heavier liquid paraffinic wax compound.

15. The process of claim 13 further comprising conveying said slurry via a distribution pipeline or a transport vehicle.

16. The process of claim 13, wherein said reactor effluent further comprises a gas phase.

17. The process of claim 16 further comprising separating said gas phase from said reactor effluent before fluidizing said solid particle medium with said reactor effluent.

18. The process of claim 13, wherein solid particle medium displaces said solid wax particles from said heat transfer surface.

19. The process of claim 13, wherein said heat transfer surface is a wall of a heat transfer tube having a tube interior, a tube exterior, a tube inlet and a tube outlet.

20. The process of claim 19, wherein said heat transfer tube is enclosed within a heat transfer shell having a shell interior, wherein said shell interior and said wall define said tube exterior, and wherein a heat transfer medium is maintained in said shell interior.

21. The process of claim 19, wherein said reactor effluent is conveyed through said tube interior.

* * * * *